(12) United States Patent
Kirn et al.

(10) Patent No.: US 12,262,916 B2
(45) Date of Patent: Apr. 1, 2025

(54) BREAST IMPLANT REMOVAL DEVICE AND RELATED METHODS

(71) Applicant: Kirn Medical Design, LLC, Lexington, KY (US)

(72) Inventors: David S. Kirn, Lexington, KY (US); Kevin J. Maudsley, Lexington, KY (US)

(73) Assignee: Kirn Medical Design, LLC, Lexington, KY (US)

( * ) Notice: Subject to any disclaimer, the term of this patent is extended or adjusted under 35 U.S.C. 154(b) by 490 days.

(21) Appl. No.: 16/219,308

(22) Filed: Dec. 13, 2018

(65) Prior Publication Data

US 2019/0388118 A1  Dec. 26, 2019

Related U.S. Application Data

(60) Provisional application No. 62/695,418, filed on Jul. 9, 2018, provisional application No. 62/687,288, filed on Jun. 20, 2018.

(51) Int. Cl.
*A61B 17/50* (2006.01)
*A61F 2/12* (2006.01)

(52) U.S. Cl.
CPC .............. *A61B 17/50* (2013.01); *A61F 2/12* (2013.01); *A61B 2217/005* (2013.01)

(58) Field of Classification Search
CPC .......... A61B 17/3468; A61B 2217/005; A61B 2017/00796; A61B 10/0283; A61B 17/08;

(Continued)

(56) References Cited

U.S. PATENT DOCUMENTS 6,237,791 B1  5/2001  Beck et al.
8,231,527 B2 * 7/2012 Beckman ........... A61B 17/0293
600/206

(Continued)

FOREIGN PATENT DOCUMENTS

WO  WO-2018226726 A1 * 12/2018 ............... A61F 2/12

OTHER PUBLICATIONS

Naseem, S. et al., "Use of a bladder syringe to evacuate ruptured breast implants: a neat approach" Ann R Coll Surg Engl 2019; 101: 133-134.

(Continued)

*Primary Examiner* — Thomas Sweet
(74) *Attorney, Agent, or Firm* — Michael S. Hargis; Stites & Harbison PLLC

(57) ABSTRACT

A device for removing a breast implant, fill material, and/or a capsule from a patient is provided. The device includes a housing having a distal portion and a proximal portion, and a suction port. Together, the distal and proximal portions define an interior chamber for receiving the breast implant. A ring is attached to an end of the proximal portion and the ring and the end of the proximal portion define an orifice through which the breast implant passes during removal. A related method includes the steps of exposing the breast implant and fill material, positioning a ring attached to an end of a housing against the exposed breast implant and fill material, the ring and the end of the housing defining an orifice through which the breast implant passes during removal, and applying suction to the housing sufficient to draw the breast implant through the orifice.

14 Claims, 6 Drawing Sheets

(58) Field of Classification Search
CPC ......... A61B 2039/0223; A61B 17/0293; A61F 2/12; A61F 13/0216; A61M 1/009; A61M 1/0001; A61M 1/007; A61M 39/0247; A61M 2039/0261; A61M 2039/0223; A61M 2039/0232; A61M 2039/0009
See application file for complete search history.

(56) References Cited

U.S. PATENT DOCUMENTS

| | | | |
|---|---|---|---|
| 2005/0119617 A1 | 6/2005 | Stecker et al. | |
| 2013/0296879 A1* | 11/2013 | Lazeroms | A61N 1/0587 606/129 |
| 2014/0228843 A1* | 8/2014 | O'Donnell | A61B 18/1492 606/48 |
| 2015/0018652 A1* | 1/2015 | Idowu | A61B 17/3423 600/323 |

OTHER PUBLICATIONS

O'Neill, J.K. et al. "A novel method to remove silicone gel after breast implant rupture" 2006 The British Association of Plastic Surgeons, published by Elsevier Ltd., pp. 889-891.

Hwang, Yang et al. "How to do the bottle suction method for removal of a silicone gel breast implant" ANZ J Surg 89 (2019) 758-759.

Pizzonia, Giuseppe et al. "An adapted suction technique to aid removal of ruptured silicone implants" JPRAS Open 20 (2019) 92-93.

Bell, Michael S. et al. "Removal of silicone breast implants and review of literature" Can J Plast Surg vol. 17 No. 4 Winter 2009;17(4):e48-e49.

Ragoowansi, R. "'The silicone siphon'—A safe and simple method of removing silicone implant and content from the breast" Journal of Plastic, Reconstructive & Aesthetic Surgery (2018) 71, 1372-1373.

O'Neil et al. "A novel method to remove silicone gel after breast implant rupture," The British Association of Plastic Surgeons. Published by Elsevier Ltd. Aug. 2006 pp. 889-891.

* cited by examiner

BREAST IMPLANT REMOVAL DEVICE AND RELATED METHODS

This application claims the benefit of U.S. Provisional Patent Application Nos. 62/687,288, filed Jun. 20, 2018, and 62/695,418, filed Jul. 9, 2018, the disclosures of which are incorporated herein by reference.

FIELD OF THE INVENTION

This document relates generally to breast prostheses or implants, and more specifically with the removal of breast implants.

BACKGROUND OF THE INVENTION

Breast implants, also known as breast prostheses, have been successfully utilized since the 1960's. The implants consist of an outer elastomeric shell and a fill material. In most implants, the fill material is a silicone polymer. From time to time, it may become necessary to remove a breast implant. The most often encountered reason for doing so is a malfunction of the implant, for example, a leak of the silicone fill material outside of the outer shell.

As time progresses, the outer elastomer shell of some breast implants may deteriorate allowing the fill material to leak out. This process is commonly known as gel bleed. In other circumstances, a frank disruption of the outer elastomeric shell occurs leading to direct leakage of the fill material. Other circumstances can also be indications for implant removal including, but not limited to, capsular contracture, implant malposition, a patient's desire for size change, and/or a patient's desire for implant removal.

Regardless of the indication for removal, actually removing a breast implant from a scar pocket, commonly known as a capsule, which naturally forms and surrounds the breast implant can present a technical and often time-consuming challenge in the operating room. More specifically, the breast implant must be brought out through a small opening in the scar pocket and skin and, preferably, removed intact. Grasping the implant digitally or with an instrument such as a clamp can lead to, or enlarge, an existing tear in the outer elastomeric shell of the implant. This is particularly true in cases of ruptured or leaking implants where the outer shell can be extremely fragile and/or partially or fully disintegrated. In such cases, removal of a ruptured or leaking breast implant and leaked material can require significant amounts of operating room time to complete.

The difficulty of removal is exacerbated by the fill material, which is commonly a silicone polymer and has a tendency to adhere to everything including, for example, breast tissue, skin, surgeon's gloves, and/or surgical instruments. As such, the silicone fill material is difficult to work with and contain and requires a significant effort to clean from breast tissue and surgical instruments. Further complicating matters, fill material or gel left within the breast pocket can lead to granuloma formation which can create palpable and visible irregularities.

In one attempt to overcome the above-noted issues relating to removal of a leaking or ruptured breast implant, a liter saline bottle is utilized as a housing for receiving the removed implant. Specifically, an incision smaller than a mouth of the bottle is made in a breast capsule. The mouth of the bottle is extended through an incision in the skin and positioned over the incision in the capsule and, subsequently, a vacuum is applied at an opposite end of the bottle. The vacuum pressure is intended to draw the breast implant, including any free fill material from a ruptured or leaking breast implant, through the incisions and into the bottle. Subsequent to removal of the implant, a pocket within the capsule is packed with a sponge to assist in removal of the capsule, i.e., to assist in the performance of a capsulectomy.

While this relatively crude device is often sufficient to remove the breast implant and any free fill material, certain issues remain. First, placement of the mouth of the bottle over the smaller incision makes forming and maintaining a vacuum seal difficult for the user. Even when a successful seal is initially formed, the initial seal is easily broken during the removal process. This is primarily due to the unrestrained nature and resulting unpredictable movement of the mouth, or end, of the bottle.

In other words, the mouth of the bottle is not secured within either incision allowing the mouth to move freely during the procedure. Such movement can be caused by the user, forces associated with the vacuum created within the bottle, and/or retentive forces caused by the implant encountering the incision in the capsule and possibly the incision in the skin. Frequently, the capsule is inelastic and at times calcified making the capsule hard and brittle such that the capsule incision may not open sufficiently to allow for simple egress of the breast implant and fill material.

The movement of the bottle is further exacerbated by the collapsing nature of the bottle sidewalls which make grasping the bottle during the procedure difficult at best. The result is often a need for multiple attempts to remove the breast implant, including any leaked fill material, and the potential spreading of leaked fill material within the surgical area. Depending on the size of the incision in the patient's skin, there is further risk of tearing the incision due to the uncontrolled evacuation of the implant unless an oversized incision is utilized in which case maintaining the initial seal is made more difficult. This combination of issues can result in inconsistent results and possibly unnecessary harm to the patient.

Accordingly, a need exists for a device and related method of efficiently and consistently removing an intact breast implant, a ruptured or leaking breast implant and leaked fill material, an intact breast implant and capsule, and/or a ruptured or leaking breast implant, leaked fill material, and capsule without further harm to the patient. The ability to remove the breast implant from the device subsequent to removal from the patient would provide the added benefit of allowing for inspection of the removed implant and identification of any markings thereon or to determine its volume.

SUMMARY OF THE INVENTION

In accordance with the purposes and benefits described herein, a device for removing a breast implant, fill material, and/or a capsule from a patient is provided. The device includes a housing having a distal portion and a proximal portion. Together, the distal and proximal portions define an interior chamber for receiving the breast implant, fill material, and/or capsule. A ring is attached to an end of the proximal portion and the ring and the end of the proximal portion define an orifice through which the breast implant, fill material, and/or capsule pass during removal. The device further includes a suction port.

In another possible embodiment, the ring includes a rolled inner edge providing a substantially smooth ingress for the breast implant and fill material.

In still another possible embodiment, the ring includes a rolled outer lip.

In yet another possible embodiment, a neck is formed between the ring and the end of the proximal portion.

In one other possible embodiment, the neck extends the ring a distance from the end of the proximal portion.

In yet still another possible embodiment, the proximal portion and the distal portion are separable.

In another possible embodiment, the proximal portion and the distal portion are shaped to accommodate nesting one within the other when not in use.

In still one other possible embodiment, the distal and proximal portions of the housing each include a solid wall.

In one additional possible embodiment, the device further includes one of a vacuum pump, a syringe, and a hand operated pump.

In one additional embodiment, a method of removing a breast implant and fill material from a patient includes the steps of: exposing the breast implant and fill material; positioning a ring attached to an end of a housing against at least one of the exposed breast implant and fill material, the ring and the end of the housing defining an orifice through which the breast implant and fill material pass during removal; and applying suction to the housing sufficient to draw the breast implant and fill material through the orifice.

In another possible embodiment, the step of exposing the breast implant includes the step of making an incision in the patient's skin and an incision in a capsule at least partially surrounding the breast implant and fill material.

In yet another possible embodiment, the step of positioning the ring against at least one of the exposed breast implant and fill material includes inserting the ring through the incision in the patient's skin and the incision in the capsule.

In still another possible embodiment, the step of positioning the ring against at least one of the breast implant and fill material includes the step of positioning the ring such that edges created by the incision in the patient's skin rest along an outer lip of the ring during removal of the breast implant and fill material.

In one other possible embodiment, the step of positioning the ring against at least one of the breast implant and fill material includes the step of positioning the ring such that edges created by the incision in the capsule rest along an outer lip of the ring during removal of the breast implant.

In an additional embodiment, a device for removing a breast implant, fill material, and/or a capsule from a patient includes a housing for receiving the breast implant, fill material, and/or capsule, a ring, and a suction port. The ring has a rolled inner edge and outer lip and is attached to an end of the housing. The ring and the end of the housing define an orifice through which the breast implant, fill material, and/or capsule pass during removal.

In another possible embodiment, the device further includes a neck formed between the ring and the end of the housing.

In yet another possible embodiment, the neck extends the ring a distance from the end of the housing.

In still another possible embodiment, the housing includes proximal and distal portions which are separable and, in still one other possible embodiment, the proximal portion and the distal portion are shaped to accommodate nesting one within the other when not in use.

In still one other possible embodiment, the distal and proximal portions of the housing each include a solid wall.

In the following description, there are shown and described several preferred embodiments of a device for removing a breast implant, fill material, and/or a capsule and related methods of removing the breast implant and fill material. As it should be realized, the devices and methods are capable of other, different embodiments and their several details are capable of modification in various, obvious aspects all without departing from the methods and devices as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the invention and together with the description serve to explain certain principles thereof. In the drawing figures.

Reference will now be made in detail to the present preferred embodiments of the device and related methods for removing a breast implant, fill material, and/or a capsule from a patient, examples of which are illustrated in the accompanying drawing figures, wherein like numerals are used to represent like elements.

DETAILED DESCRIPTION

Figure 1:
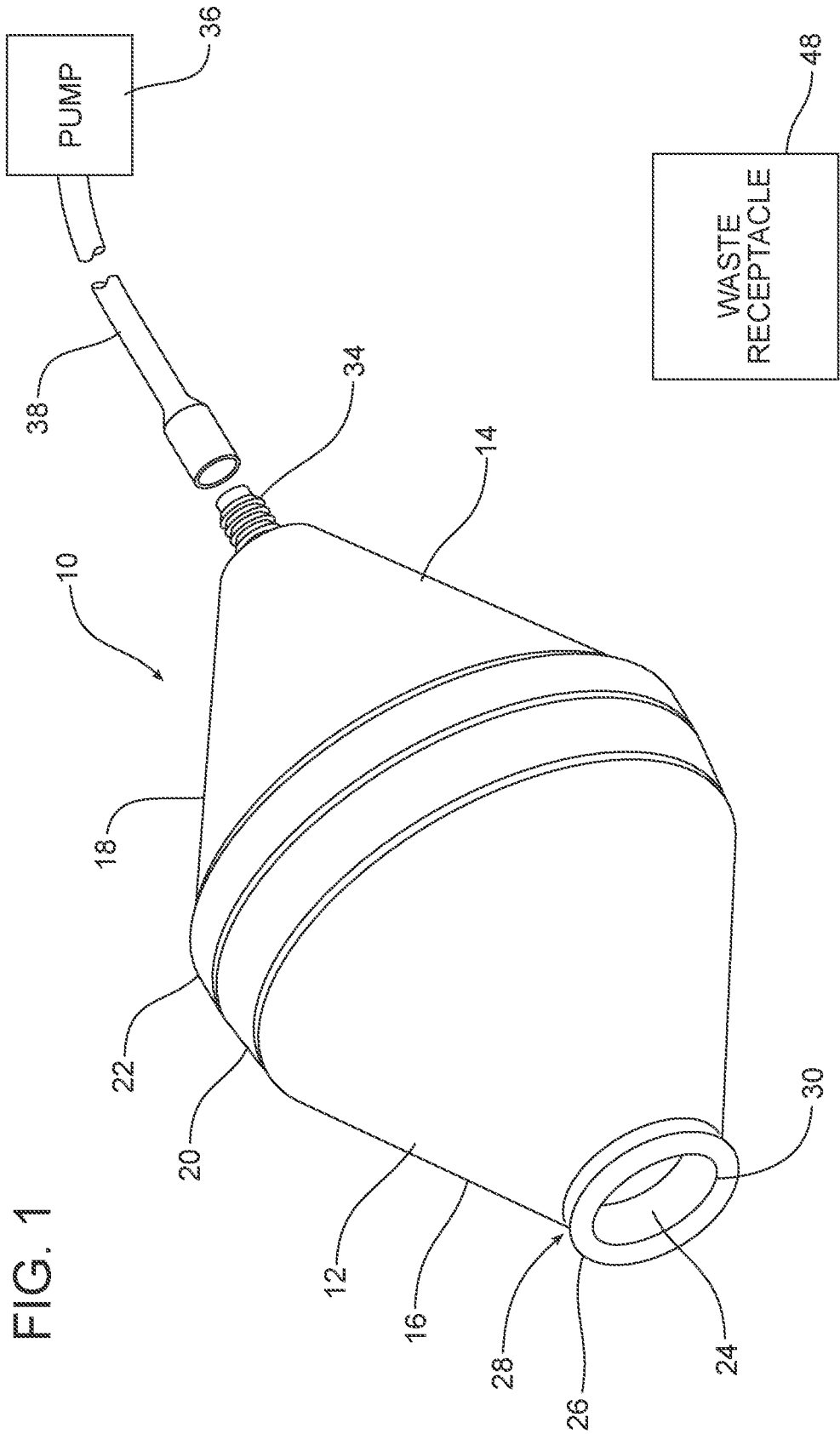
FIG. 1 is a perspective view of a device for removing a breast implant, fill material, and/or a capsule from a patient.

Reference is now made to FIG. 1 which illustrates a device 10 for removing a breast implant (I) from a patient. The breast implant may be removed intact or when leaking fill material, and with or without a capsule which naturally forms at least partially around breast implants. References to breast implants within this specification refer to the breast implant including the outer elastomeric shell and the fill material, whether the shell is intact or the till material has leaked out of the shell, and/or the capsule. In other words, a reference to contacting the breast implant (I) includes contacting the fill material if leaked out, the outer shell, and/or the capsule unless otherwise indicated.

The device 10 consists of a first, proximal portion 12 and a second, distal portion 14 which together form a housing. In the described embodiment, the proximal and distal portions are generally halves which are separable. Each portion 12, 14 consists primarily of a solid wall 16, 18 and together define an interior chamber for receiving the breast implant (I). Other embodiments of the device 10, however, may include a unitary housing wherein the proximal and distal portions are not separable.

Each of the proximal and distal portions 12, 14 are generally frustoconical in shape, in the described embodiment, and join together to form the housing along base ends 20, 22. Of course, other shapes (e.g., round, oval, oblong, conical, at least partially cylindrical, etc.) may be utilized and the portions may take different shapes. Overall, any shape may be utilized, and the shape of the proximal and distal portions 12, 14 should be selected to accommodate the volume of the breast implant (I) and provide sufficient mechanical strength to maintain a stable shape and avoid a collapse of the device 10 under vacuum pressure. In other words, the phrase solid wall refers to a wall of sufficient strength and/or rigidity, regardless of shape, to avoid collapse under a vacuum pressure, which is the driving force for removal or extraction of the breast implant, sufficient to remove or extract the breast implant (I).

The total volume of the interior chamber, adding both proximal and distal portions 12, 14 together, should be sufficient to remove large-sized breast implants. In other words, the volume of the chamber is at least 600 cc capacity or greater, in the described embodiment, to accommodate the removal of large-sized breast implants. Of course, other embodiments may utilize smaller chamber volumes and/or specifically sized chamber volumes on a patient to patient basis.

Figure 2:
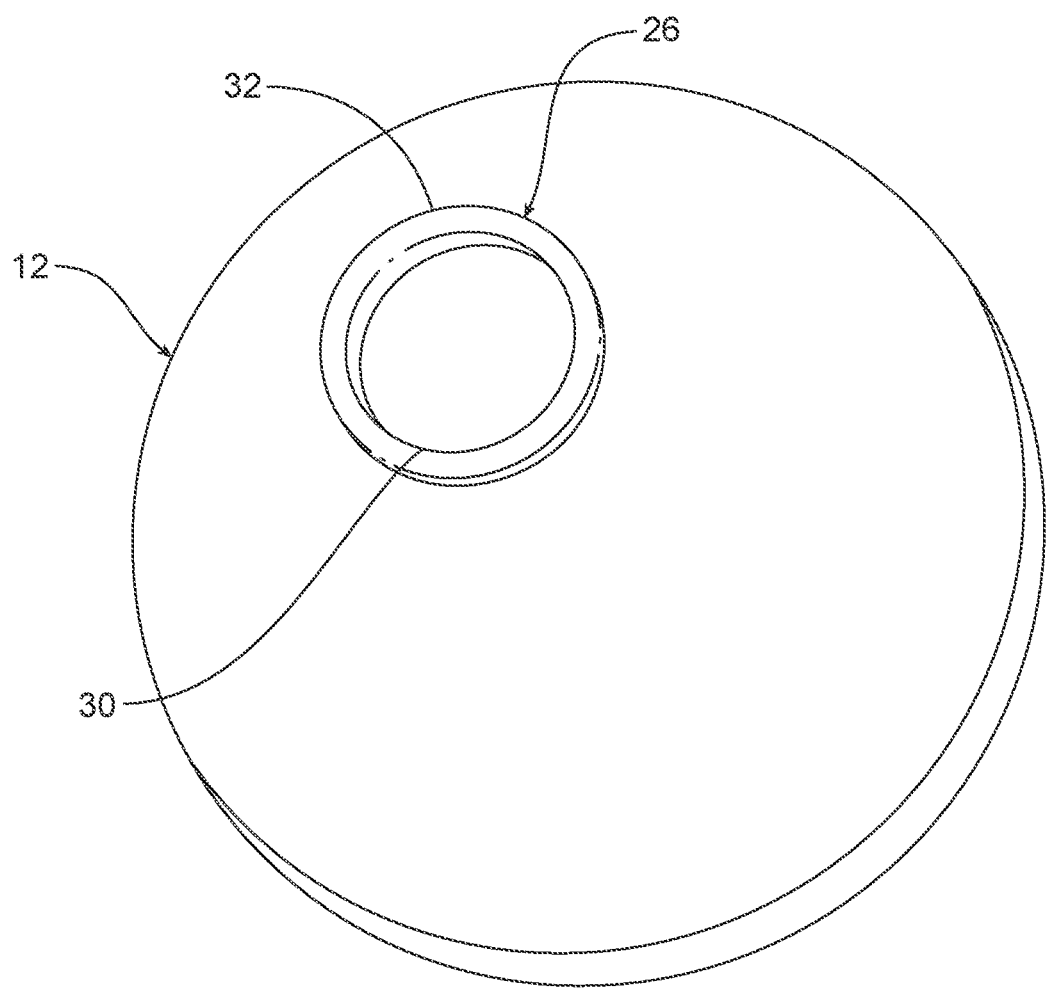
FIG. 2 is a perspective view of an end of the breast implant, fill material, and/or capsule removal device showing a ring having a rounded lip attached to an end of the proximal portion of the housing.
Figure 3:
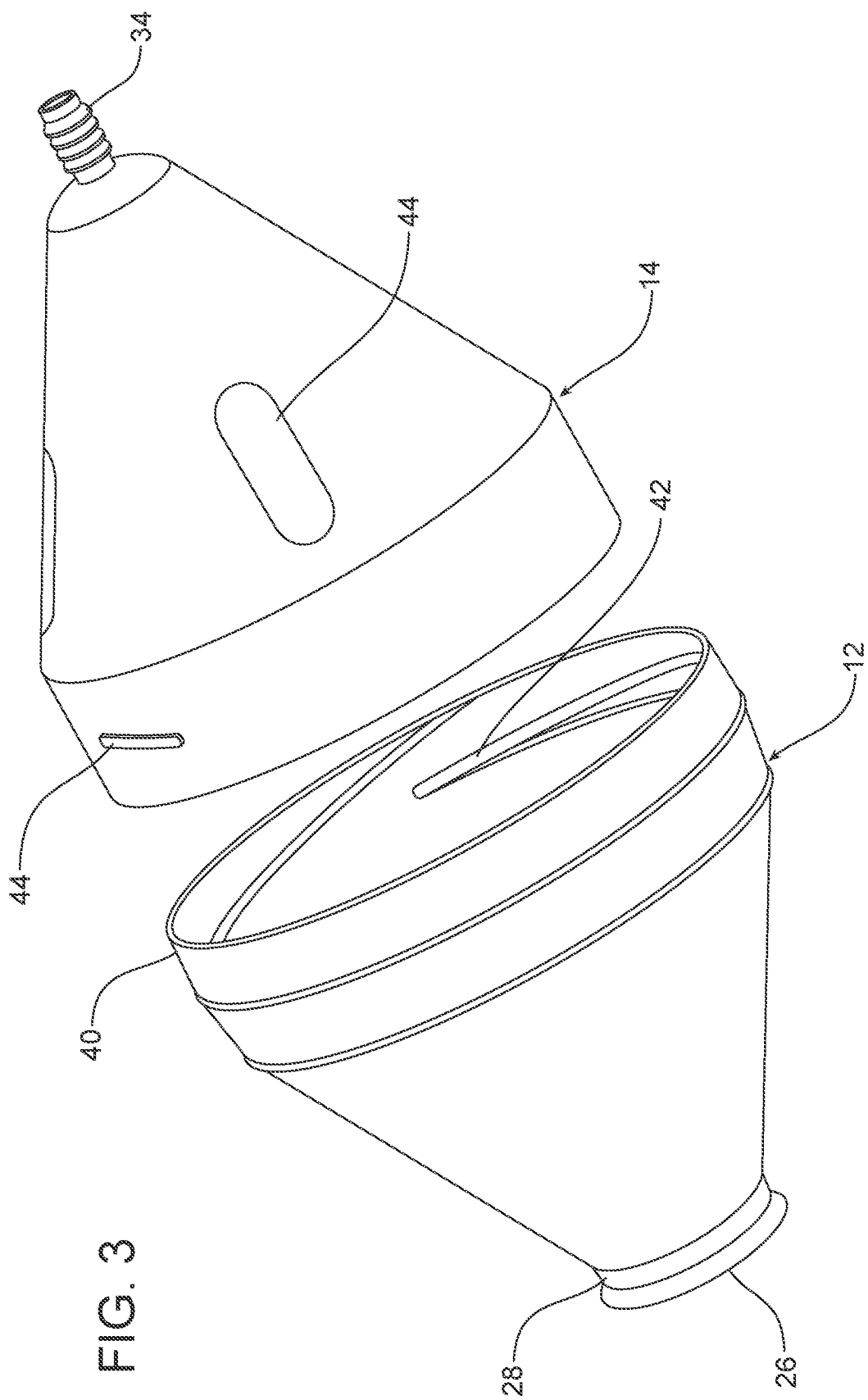
FIG. 3 is a perspective view of a side of the breast implant, fill material, and/or capsule removal device shown in a partially disassembled state.

In the described embodiment shown in FIGS. 1-3, the housing includes an integrally formed ring 26 that is fixed in position, extended from the proximal portion 12 of the housing. More specifically, as best shown in FIG. 3, a neck 28 is formed between the proximal portion 12 of the housing and the ring 26 which extends the ring a distance from a proximal end of the proximal portion 12. The ring 26, neck 28, and proximal end of the proximal portion of the housing together define an orifice 24 through which the breast implant (I) passes during removal. In other embodiments, the neck 28 may extend the ring a negligible or no distance at all from the proximal end of the proximal portion of the housing such that the ring and proximal end generally define the orifice.

The ring 26 is positioned in contact with the breast implant (I) during the removal process such that a seal is formed between the housing and the breast implant sufficient to allow vacuum pressure to draw the breast implant from the patient, through the incision and orifice simultaneously, and into the housing. In effect, the ring 26 and neck 28 function as a retractor within the skin and/or capsule incisions. This positioning aids in maintaining the initial seal formed between the ring 26 and the breast implant (I) and protects the incision(s) from unwanted tearing as the implant passes through the incision(s) but within the device 10.

In other words, the rigidness of the ring 26 causes the breast implant (I) to alter its shape as it enters the device 10 rather than the implant or capsule being pulled through the incisions without altering shape. Depending on the patient, the capsule may calcify over time becoming hard and brittle or may be thick and inelastic limiting the elasticity of the capsule incision and the ability to accommodate egress of the breast implant. Positioning the ring 26 and neck 28 within the capsule incision avoids any issues relating to the elasticity of the capsule.

As shown, the described ring 26 includes a rolled inner edge 30 and defines an outermost diameter of the orifice 24 in one embodiment. In other words, the rolled inner edge 30 defines a diameter of the orifice 24 first encountered by the breast implant (I). Other embodiments may not utilize a ring and the proximal end of the proximal portion itself may define the outermost diameter of the orifice. The rolled inner edge 30 provides a substantially smooth and mechanically advantageous ingress for the breast implant (I) being removed. The ring 26, including the rolled inner edge 30, may be made of a lubricious material or a medical lubricant may be applied thereto to limit friction between the breast implant (I), possibly leaked/leaking fill material (M), and the rolled inner edge as the implant passes through the orifice 24 during the removal process.

The described ring 26 also includes a flared, rounded, or rolled outer lip 32 as shown in FIGS. 1 and 3. The outer lip 32 helps to assist with a smooth insertion of the ring 26 into an incision in the patient's skin (D) and a capsulotomy incision. Further, the outer lip 32 assists with retention of the device 10 within the incision(s) and maintains edges of the incision(s) in an open position when the ring 26 is positioned in contact with the breast implant (I) during removal. In other words, the ring 26 is inserted through the incision(s) and positioned such that the ring is contacting the breast implant (I). In this position, the incision edges extend around the outer lip 32 and rest around or behind the ring 26 which is generally adjacent the neck 28. While the ring 26 and defined orifice are described as round in one embodiment, the ring and/or orifice may take essentially any shape including, for example, oval or oblong. Even more, the outer lip 32 may include a flat portion 33 adjacent the neck 28 as shown in FIG. 4 to further aid in maintaining the device 10 in position.

As shown in FIGS. 1 and 3, a suction port 34 extends from the distal portion 14 of the housing in the described embodiment. The suction port 34, however, may be positioned in any location on the housing. The suction port 34 is a nipple or barbed connector, in the described embodiment, designed to receive tubing connected to a suction source 36 (e.g., a vacuum pump, a syringe, and/or a hand operated pump). Various other connectors may be used to connect the device 10 to a suction source as is known in the art. In the described embodiment, the suction source 36 is a vacuum pump. Operating rooms typically provide a suction source which may be a vacuum pump located in a remote area or within the operating room itself. In some instances, portable vacuum pumps, syringes, or even hand operated pumps may be supplied with the device 10 for utilization in operating rooms which are void of a suitable suction source. In each instance, however, the device 10 is connected to the suction source 36 utilizing tubing 38 as shown in FIG. 1.

Figure 4:
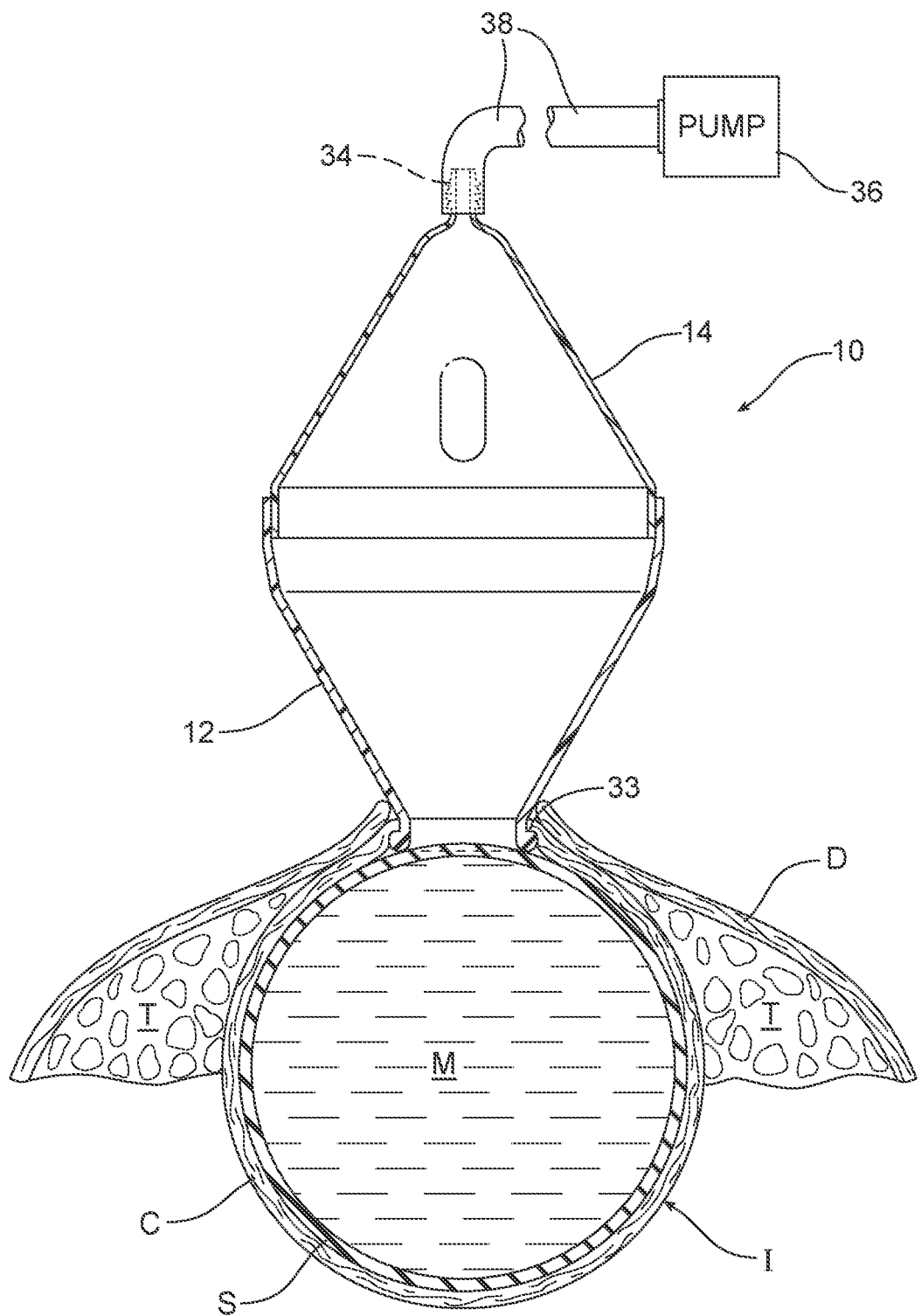
FIG. 4 is a cross sectional view of the breast implant, fill material, and/or capsule removal device showing the ring attached to the housing in contact with an intact breast implant at an initial stage of the implant removal process.

At a distal end 32 of the distal half 14, shown in FIGS. 1 and 4, a nipple or barbed connector 34 receives a hose (not shown) to provide vacuum pressure for use in removal and/or forced air for use in the insertion process. Vacuum and air sources and/or hoses are universally available for surgical procedures in operating rooms. In alternate embodiments, a tube or hose may extend from the housing with the connector attached thereto for mating with a vacuum/fluid hose or vacuum/fluid source connector.

Figure 5:
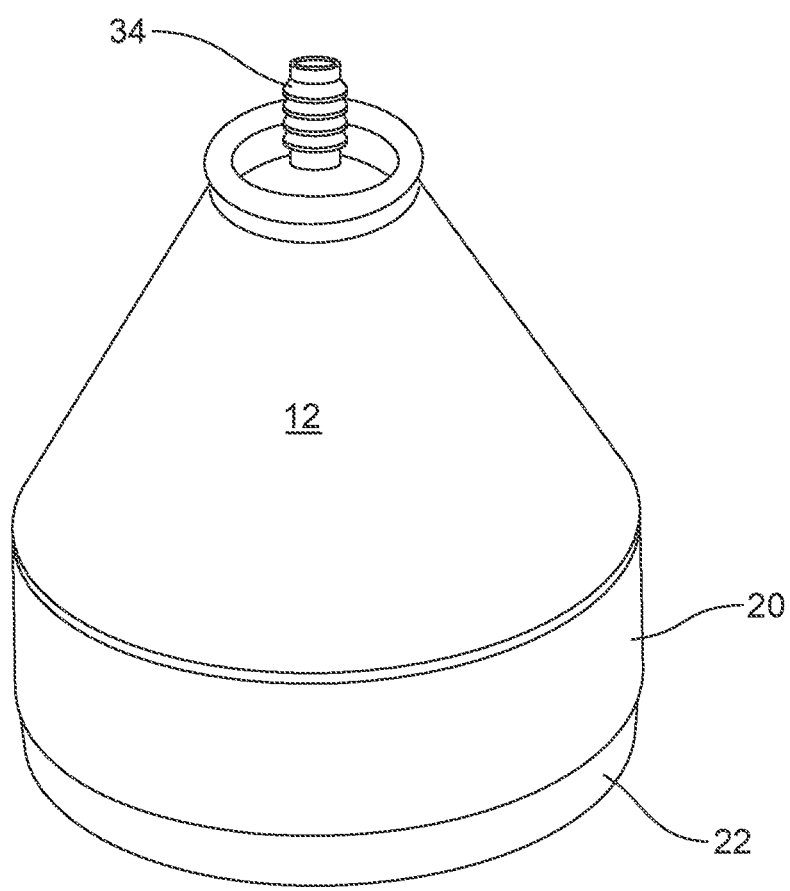
FIG. 5 is a perspective view of first and second portions of the breast implant, fill material, and/or capsule removal device in a nested position.

As shown and noted above, the proximal and distal portions 12, 14 are separable and generally frustoconical in shape in the described embodiment. This shape, and others, accommodate nesting of the portions one within the other when not in use as shown in FIG. 5. In the described embodiment, the suction port 34 extends through the orifice 24 when the distal and proximal portions are in the nested position. Nesting the portions in general is particularly useful for packaging the preoperative device 10. Of course, other shapes may be utilized so long as they provide sufficient mechanical rigidity to avoid collapse under vacuum pressure or the device may be a unitary structure as described above. In addition, the distal and proximal portions may be designed or a spacer inserted therebetween during shipping such that the suction port 34 extends within but not through the orifice 24 or does not extend within the orifice at all.

As further shown in FIG. 3, the proximal portion 12 and the distal portion 14 are connected by cooperating threads in the described embodiment. The connection between the two portions 12, 14 provided by the threads is sufficient to maintain vacuum pressure and also prevent leaking of any silicone polymer fill material received within the device 10. More specifically, a distal end 40 of the proximal portion 12 has a screw thread 42 that combines with a mating screw thread 44 of the distal portion 14 forming a connection that allows the two portions to be pulled together when vacuum pressure is applied. Of course, other types of mechanical connections may be utilized in lieu of the threaded mechanism in alternate embodiments such as, but not limited to, press fit connections, friction fit connections, butt connections with a separate connection ring, or a compression band with each sufficient to maintain the two portions 12, 14 in substantially parallel alignment to ensure a good seal. Further, gaskets or O rings may be utilized in all such embodiments to further ensure a good seal or the above-described unitary design may be utilized.

As an added convenience, one or more grips 46 may be provided on one or both of the proximal and distal portions 12, 14 to assist the user in assembly and disassembly thereof. As best shown in FIGS. 3 and 4, the grips 46 may be detents formed in the one or both portions 12, 14. While shown as generally oval in shape in the described embodiment, the grips 46 may take any shape sufficient to provide improved gripping of the portions 12, 14 during use and/or assembly/disassembly. Even more, the grips may be elevated (not shown) extending above an outer surface of the housing. The elevated grips may be made of a rubber or like material and may provide a rigid and/or a tacky feel for the user. Of course, other types and numbers of grips may be utilized in alternate embodiments.

Figure 6:
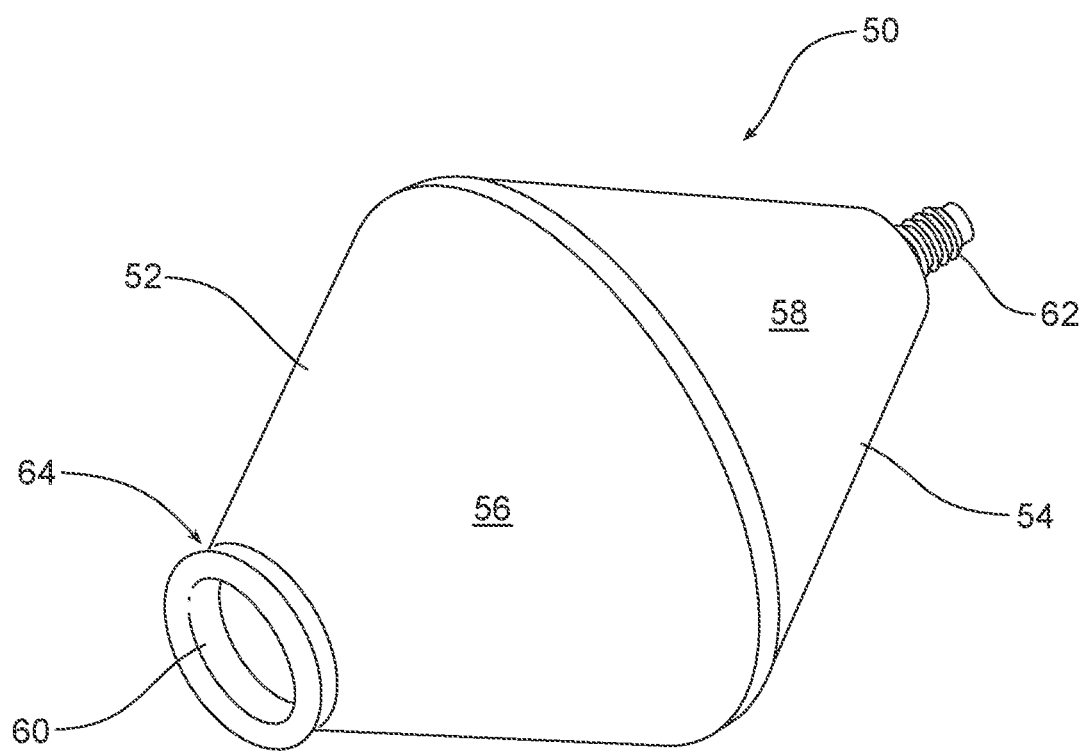
FIG. 6 is a perspective view of an alternate embodiment of a unitary breast implant, fill material, and/or capsule removal device.

As noted above, a device 50 may be a unitary structure as shown in FIG. 6. In other words, the device 50 may be a single piece unit thereby eliminating threaded mechanism 36 between the proximal and distal portions 12, 14 of the earlier described device 10. The alternate device 50 similarly includes proximal and distal portions 52, 54 which define an interior chamber, and generally includes solid walls, 56, 58, a defined orifice 60, a suction port 62, and a ring 64 in at least the described embodiment. Other than the unitary nature of the housing, the device 50 is the same as the above described embodiment and alternative embodiments thereof. Even more, the unitary device 50 is intended for disposal after a single use.

In all embodiments, caps (not shown) may be provided to seal off the proximal opening and/or distal suction port prior to and/or post operation. In addition, the devices 10, 50 may be created using materials suitable for biohazardous waste disposal.

The method of removing a breast implant (I) of a patient referred to above in describing devices used therein includes the steps of exposing the breast implant, positioning a ring of the device in contact with the breast implant, and applying suction to the device sufficient to draw the breast implant through an orifice. The method is further described with reference to an embodiment of the device 10 described above.

The device 10 is supplied in a sterile condition. The user first assembles the two portions 12, 14 of the device 10 together using the threaded mechanism 36. Once together, the device 10 is ready for use. Surgically, a capsule (C) which naturally forms at least partially around the breast implant (I) is exposed via incisions through skin (S), breast tissue (T), and muscle, collectively the skin incision, depending on the placement of the breast implant. If a partial or total capsulectomy procedure is to be completed, the desired steps may be performed prior to or after removal of the breast implant (I). In such a scenario, the capsule or partial capsule typically accompanies the breast implant (I) into the device 10 as further described below.

As part of the described removal process, a capsulotomy incision is created in the capsule (C) thereby directly exposing the breast implant (I). The capsulotomy incision is necessarily sized large enough to admit the ring 26 in the described method. This allows for direct contact between the device 10 and the breast implant (I) which necessarily includes the outer shell (S) and/or fill material (M) if the outer shell of the breast implant (I) has dissolved or is disrupted. More specifically, the ring 26 of the device 10 is positioned in contact with the breast implant.

In the described method, the ring 26 defines at least a portion of the orifice and is positioned in contact with the breast implant (I) by inserting the ring through the incisions in the patient's skin (D) breast tissue (T) and capsule (C). With the ring 26 inserted through the incision in the patient's skin (D) and capsule (C) and positioned in contact with the breast implant (I), the outer lip 30 of the ring 26 assists with retention of the device 10 within the incision(s) and functions as a retractor by maintaining edges of the incision(s) in an open position. In other words, edges created by the incision in the patient's skin (D) extend around the outer lip 32 and rest behind the ring 26 during removal of the breast implant (I). Again, if an incision is made in the capsule (C), then edges of the capsule incision likewise rest behind the ring 26. Even more specifically, edges of the incision(s) rest in a recess behind the ring 28 which is generally adjacent the neck 28.

Subsequent to inserting the ring 26 and positioning the orifice 24 in contact with the breast implant (I), a suction source 36 is connected to the suction port 34. As described above, the suction port 34 may be a nipple or barbed connector 34 which is positioned at the distal end of the distal portion 14 of the device 10. In the described embodiment, tubing 38 is utilized to connect the suction port 34 to the suction source 36. Again, the suction source 36 may be a vacuum pump 36 provided with the device 10 or located in an operating room or in a basement of a building wherein the operating room is located. In alternative embodiments, a syringe or hand operated vacuum source may be utilized as the suction source. In other words, a suction source may be provided with the device or an existing suction source may be utilized by connecting the device thereto.

Once connected, the suction source 36 is initiated applying suction to the housing sufficient to draw the breast implant (I) through the orifice. In other words, the suction source 36 is initiated drawing air out of the internal chamber of the device 10 through the tubing 38. The negative pressure created by the vacuum draws the implant (I) through the orifice 26 and into the internal chamber of the device (10). For reference, the breast implant (I) being removed will move along a proximal to distal direction during the removal process.

The natural cohesivity of the implant (I) including its outer shell (S) and fill material (M) ensure that the entire implant, including any leaked fill material or gel, is drawn into the interior chamber of the housing. In addition, if the capsule (C) has been fully mobilized from its surrounding soft tissue attachments prior to removal of the implant (I), the capsule typically accompanies the breast implant (I) into the interior chamber. In other words, the suction applied to the housing is sufficient to draw the breast implant (I) and the capsule (C) through the orifice. In such a scenario, the capsule (C) may not be breached and the ring 26 may be inserted through the incision in the patient's skin (D) and positioned in contact with the capsule.

It should be noted that the suction source 36 can be connected to the suction port 34 prior to insertion of the ring 26 and/or positioning of the orifice in contact with the breast implant (I) or capsule (C). Similarly, the suction source 36 may be initiated at any time throughout the process.

If the user desires to inspect the breast implant (I) now contained in the interior chamber of the device 10, then the proximal and distal portions 12, 14 may be separated opening the device and granting access to the breast implant. If the breast implant (I) is intact, it may be removed from the interior chamber for further inspection and/or disposal into a suitable biohazardous waste receptacle 48. The two portions 12, 14 of the device 10 may then be reassembled, and the same device may be used to remove a contralateral breast implant, if desired.

In the event the breast implant (I) is ruptured or there has been substantial gel bleed, it is recommended not to remove the breast implant from the interior chamber as doing so may expose the operative field to the sticky polymer fill material (M) or gel. Rather, the breast implant (I) and device 10 may be disposed of within the biohazardous waste receptacle 48 with or without caps applied to the ring 26 and/or distal suction port 34 as desired to seal the breast implant (I) within the interior chamber. A new removal device 10 may be used for extraction of the contralateral breast implant. In the event the one-piece alternate embodiment of the device 50 is utilized, it is preferable to use one removal device 50 per breast implant (I). In this scenario, the breast implant (I) resident in the interior chamber of the device 50 may not be taken out for inspection or otherwise.

The foregoing has been presented for purposes of illustration and description. It is not intended to be exhaustive or to limit the embodiments to the precise form disclosed. Obvious modifications and variations are possible in light of the above teachings. For instance, the integrally formed ring that is fixed in position and extends from the proximal portion of the housing may not be integrally formed. The ring and a neck section extending therefrom may be attached to the end of the proximal portion 12 of the device 10. For example, the ring and neck section may be screwed into the proximal portion 12 such that removal is possible. In this manner, the ring may extend any desired distance from the proximal portion 12 subject only to the length of the neck.

In another possible modification, if a partial or total capsulectomy procedure is to be completed, the desired procedure may be performed prior to or after removal of the breast implant (I). Even more, the above-described devices may be sized to accommodate two breast implants such that removal of a first removed implant prior to removal of a contralateral implant or utilization of two devices is unnecessary. All such modifications and variations are within the scope of the appended claims when interpreted in accordance with the breadth to which they are fairly, legally and equitably entitled.

What is claimed:

1. A device for removing a breast implant, fill material, and/or a capsule from a patient, comprising:
    a housing having solid distal and proximal portions which together define an interior chamber for receiving the breast implant, fill material, and/or capsule;
    a ring fixed in position to an end of the proximal portion, the ring defining a rigid orifice through which the breast implant, fill material, and/or capsule pass during removal, and including a rounded outer lip having an outer diameter greater than an outer diameter of the end of the proximal portion; and
    a suction port.

2. The device for removing a breast implant, fill material, and/or a capsule from a patient of claim 1, wherein the proximal portion and the distal portion are separable.

3. The device for removing a breast implant, fill material, and/or a capsule from a patient of claim 2, wherein the ring includes a rolled inner edge providing a substantially smooth ingress for the breast implant and fill material.

4. The device for removing a breast implant, fill material, and/or a capsule from a patient of claim 3, wherein an inner diameter of the rolled inner edge is substantially the same as an inner diameter of the end of the proximal portion.

5. The device for removing a breast implant, fill material, and/or a capsule from a patient of claim 2, wherein the proximal portion and the distal portion are shaped to accommodate nesting one within the other when not in use.

6. The device for removing a breast implant, fill material, and/or a capsule from a patient of claim 2, further comprising a neck between the ring and the end of the proximal portion.

7. The device for removing a breast implant, fill material, and/or a capsule from a patient of claim 6, wherein the ring includes a rolled inner edge.

8. The device for removing a breast implant, fill material, and/or a capsule from a patient of claim 7, wherein an inner diameter of the rolled inner edge is substantially the same as an inner diameter of the neck.

9. The device for removing a breast implant, fill material, and/or a capsule from a patient of claim 6, wherein the neck extends the ring a distance from the end of the proximal portion.

10. The device for removing a breast implant, fill material, and/or a capsule from a patient of claim 1, wherein the ring includes a rolled inner edge providing a substantially smooth ingress for the breast implant and fill material.

11. The device for removing a breast implant, fill material, and/or a capsule from a patient of claim 10, wherein an inner diameter of the rolled inner edge is substantially the same as an inner diameter of the end of the proximal portion.

12. The device for removing a breast implant, fill material, and/or a capsule from a patient of claim 1, wherein the solid distal and proximal portions each include a solid wall.

13. The device for removing a breast implant, fill material, and/or a capsule from a patient of claim 1, further comprising one of a vacuum pump, a syringe, and a hand operated pump.

14. The device for removing a breast implant, fill material, and/or a capsule from a patient of claim 1, wherein a neck between the ring and the end of the proximal portion extends the ring a distance from the end of the proximal portion.

* * * * *